United States Patent
Slate et al.

(10) Patent No.: US 12,186,535 B2
(45) Date of Patent: *Jan. 7, 2025

(54) SYSTEM AND METHOD FOR AN INJECTION USING A SYRINGE NEEDLE

(71) Applicant: AVANT MEDICAL CORP., Thousand Oaks, CA (US)

(72) Inventors: John B. Slate, Encinitas, CA (US); Richard J. Koerner, San Diego, CA (US); Corey M. Magers, Oceanside, CA (US); Michael W. Burk, San Marcos, CA (US)

(73) Assignee: AVANT MEDICAL CORP., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/213,555

(22) Filed: Jun. 23, 2023

(65) Prior Publication Data

US 2023/0330338 A1 Oct. 19, 2023

Related U.S. Application Data

(60) Continuation of application No. 16/832,987, filed on Mar. 27, 2020, now Pat. No. 11,724,032, which is a
(Continued)

(51) Int. Cl.
*A61M 5/20* (2006.01)
*A61M 5/315* (2006.01)
*A61M 5/32* (2006.01)

(52) U.S. Cl.
CPC .............. *A61M 5/20* (2013.01); *A61M 5/326* (2013.01); *A61M 2005/206* (2013.01);
(Continued)

(58) Field of Classification Search
CPC .. A61M 5/20; A61M 5/326; A61M 2005/206; A61M 2005/208;
(Continued)

(56) References Cited

U.S. PATENT DOCUMENTS

| 2,525,398 A | 10/1950 | Collins |
| 2,565,081 A | 8/1951 | Maynes |

(Continued)

FOREIGN PATENT DOCUMENTS

| AU | 2009249027 B2 | 8/2014 |
| CA | 2074565 C | 2/2000 |

(Continued)

OTHER PUBLICATIONS

Japanese Patent Application No. 2016-502669, Decision of Rejection, mailed Aug. 6, 2018.
(Continued)

*Primary Examiner* — Theodore J Stigell
(74) *Attorney, Agent, or Firm* — MARSHALL, GERSTEIN & BORUN LLP; Michael P. Furmanek (57) ABSTRACT

An auto-injector for injecting a fluid medicament into a patient from a pre-filled syringe requires a disposable cassette that is selectively engageable with the reusable injector. The syringe is latched onto the cassette, and the cassette is then engaged with the injector. Activation of the injector causes a first motor to move the syringe so its needle is extended from a concealed position inside the cassette for injection of the medicament. A second motor on the injector is then activated to expel fluid medicament from the syringe. Then, the first motor is again activated to withdraw the syringe into the cassette for disposal of the cassette/syringe after an injection.

15 Claims, 2 Drawing Sheets

Related U.S. Application Data division of application No. 15/440,420, filed on Feb. 23, 2017, now Pat. No. 10,639,422, which is a division of application No. 13/269,750, filed on Oct. 10, 2011, now Pat. No. 9,616,173, which is a continuation of application No. 12/178,447, filed on Jul. 23, 2008, now Pat. No. 8,052,645.

(52) U.S. Cl.
CPC ............... *A61M 2005/208* (2013.01); *A61M 2005/31588* (2013.01); *A61M 2205/50* (2013.01); *A61M 2205/6045* (2013.01)

(58) Field of Classification Search
CPC .... A61M 2005/31588; A61M 2205/50; A61M 2205/6045; A61M 2205/121
See application file for complete search history.

(56) References Cited

U.S. PATENT DOCUMENTS

| | | |
|---|---|---|
| 2,701,566 A | 2/1955 | Krug |
| 2,702,547 A | 2/1955 | Glass |
| 3,051,173 A | 8/1962 | Johnson et al. |
| 3,064,650 A | 11/1962 | Elder et al. |
| 3,203,269 A | 8/1965 | Perrine |
| 3,212,685 A | 10/1965 | James et al. |
| 3,297,210 A | 1/1967 | Lucas |
| 3,623,474 A | 11/1971 | Heilman et al. |
| 3,720,211 A | 3/1973 | Kyrias |
| 3,859,996 A | 1/1975 | Mizzy et al. |
| 3,964,481 A | 6/1976 | Gourlandt et al. |
| 4,108,177 A | 8/1978 | Pistor |
| 4,198,975 A | 4/1980 | Haller |
| 4,231,368 A | 11/1980 | Becker |
| 4,273,122 A | 6/1981 | Whitney et al. |
| 4,276,879 A | 7/1981 | Yiournas |
| 4,333,459 A | 6/1982 | Becker |
| 4,373,526 A | 2/1983 | Kling |
| 4,421,107 A | 12/1983 | Estes et al. |
| 4,465,478 A | 8/1984 | Sabelman et al. |
| 4,493,704 A | 1/1985 | Beard et al. |
| 4,502,488 A | 3/1985 | Degironimo et al. |
| 4,504,263 A | 3/1985 | Steuer et al. |
| 4,515,590 A | 5/1985 | Daniel |
| 4,573,975 A | 3/1986 | Frist et al. |
| 4,585,439 A | 4/1986 | Michel |
| 4,613,328 A | 9/1986 | Boyd |
| 4,617,016 A | 10/1986 | Blomberg |
| 4,636,201 A | 1/1987 | Ambrose et al. |
| 4,685,903 A | 8/1987 | Cable et al. |
| 4,758,227 A | 7/1988 | Lancaster et al. |
| 4,787,893 A | 11/1988 | Villette |
| 4,790,823 A | 12/1988 | Charton et al. |
| 4,838,857 A | 6/1989 | Strowe et al. |
| 4,877,034 A | 10/1989 | Atkins et al. |
| 4,902,279 A | 2/1990 | Schmidtz et al. |
| 4,919,596 A | 4/1990 | Slate et al. |
| 4,986,818 A | 1/1991 | Imbert et al. |
| 5,013,299 A | 5/1991 | Clark |
| 5,024,616 A | 6/1991 | Ogle, II |
| 5,034,003 A | 7/1991 | Denance |
| 5,080,104 A | 1/1992 | Marks et al. |
| 5,085,641 A | 2/1992 | Sarnoff et al. |
| 5,092,843 A | 3/1992 | Monroe et al. |
| 5,098,400 A | 3/1992 | Crouse et al. |
| 5,112,317 A | 5/1992 | Michel |
| 5,114,404 A | 5/1992 | Paxton et al. |
| 5,114,406 A | 5/1992 | Gabriel et al. |
| 5,176,643 A | 1/1993 | Kramer et al. |
| 5,180,371 A | 1/1993 | Spinello |
| D334,233 S | 3/1993 | Schaechter |
| 5,200,604 A | 4/1993 | Rudko et al. |
| 5,221,268 A | 6/1993 | Barton et al. |
| 5,271,413 A | 12/1993 | Dalamagas et al. |
| 5,300,029 A | 4/1994 | Denance |
| 5,318,522 A | 6/1994 | D Antonio |
| 5,352,196 A | 10/1994 | Haber et al. |
| 5,354,286 A | 10/1994 | Mesa et al. |
| 5,354,287 A | 10/1994 | Wacks |
| 5,382,785 A | 1/1995 | Rink |
| 5,393,497 A | 2/1995 | Haber et al. |
| 5,394,866 A | 3/1995 | Ritson et al. |
| 5,425,715 A | 6/1995 | Dalling et al. |
| 5,431,627 A | 7/1995 | Pastrone et al. |
| 5,451,210 A | 9/1995 | Kramer et al. |
| 5,456,670 A | 10/1995 | Neer et al. |
| 5,458,263 A | 10/1995 | Ciammitti et al. |
| 5,478,316 A | 12/1995 | Bitdinger et al. |
| 5,531,698 A | 7/1996 | Olsen |
| 5,540,664 A | 7/1996 | Wyrick |
| 5,569,190 A | 10/1996 | D Antonio |
| 5,569,197 A | 10/1996 | Helmus et al. |
| 5,569,212 A | 10/1996 | Brown |
| 5,578,014 A | 11/1996 | Erez et al. |
| 5,584,815 A | 12/1996 | Pawelka et al. |
| 5,593,390 A | 1/1997 | Castellano et al. |
| 5,599,302 A | 2/1997 | Lilley et al. |
| 5,616,132 A | 4/1997 | Newman |
| 5,647,851 A | 7/1997 | Pokras |
| 5,647,853 A | 7/1997 | Feldmann et al. |
| 5,665,071 A | 9/1997 | Wyrick |
| 5,681,291 A | 10/1997 | Galli |
| 5,690,618 A | 11/1997 | Smith et al. |
| 5,695,472 A | 12/1997 | Wyrick |
| 5,698,189 A | 12/1997 | Rowe et al. |
| 5,709,662 A | 1/1998 | Olive et al. |
| 5,720,729 A | 2/1998 | Kriesel |
| 5,728,074 A | 3/1998 | Castellano et al. |
| 5,746,714 A | 5/1998 | Salo et al. |
| 5,779,675 A | 7/1998 | Reilly et al. |
| 5,779,683 A | 7/1998 | Meyer |
| 5,807,346 A | 9/1998 | Frezza |
| 5,843,036 A | 12/1998 | Olive et al. |
| 5,868,711 A | 2/1999 | Kramer et al. |
| 5,911,703 A | 6/1999 | Slate et al. |
| 5,919,159 A | 7/1999 | Lilley et al. |
| 5,921,963 A | 7/1999 | Erez et al. |
| 5,921,966 A | 7/1999 | Bendek et al. |
| 5,928,158 A | 7/1999 | Aristides |
| 5,945,046 A | 8/1999 | Hehl et al. |
| 5,957,897 A | 9/1999 | Jeffrey |
| 5,968,063 A | 10/1999 | Chu et al. |
| 5,993,412 A | 11/1999 | Deily et al. |
| 5,993,423 A | 11/1999 | Choi |
| 6,019,745 A | 2/2000 | Gray |
| 6,019,747 A | 2/2000 | McPhee |
| 6,051,896 A | 4/2000 | Shibuya et al. |
| 6,077,055 A | 6/2000 | Vilks |
| 6,090,082 A | 7/2000 | King et al. |
| 6,099,503 A | 8/2000 | Stradella |
| 6,104,941 A | 8/2000 | Huey et al. |
| 6,149,626 A | 11/2000 | Bachynsky et al. |
| 6,159,184 A | 12/2000 | Perez et al. |
| 6,171,276 B1 | 1/2001 | Lippe et al. |
| 6,171,283 B1 | 1/2001 | Perez et al. |
| 6,183,442 B1 | 2/2001 | Athanasiou et al. |
| 6,190,361 B1 | 2/2001 | Gettig et al. |
| 6,203,530 B1 | 3/2001 | Stewart, Sr. |
| 6,210,369 B1 | 4/2001 | Wilmot et al. |
| 6,213,987 B1 | 4/2001 | Hirsch et al. |
| 6,241,704 B1 | 6/2001 | Peterson et al. |
| 6,241,709 B1 | 6/2001 | Bechtold et al. |
| 6,245,043 B1 | 6/2001 | Villette |
| 6,248,093 B1 | 6/2001 | Moberg |
| 6,270,479 B1 | 8/2001 | Bergens et al. |
| 6,270,481 B1 | 8/2001 | Mason et al. |
| 6,280,421 B1 | 8/2001 | Kirchhofer et al. |
| 6,290,683 B1 | 9/2001 | Erez et al. |
| 6,318,647 B1 | 11/2001 | Gaw et al. |
| 6,344,030 B1 | 2/2002 | Duchon et al. |
| 6,344,032 B1 | 2/2002 | Perez et al. |
| 6,371,939 B2 | 4/2002 | Bergens et al. |
| 6,387,078 B1 | 5/2002 | Gillespie, III |

(56) References Cited

U.S. PATENT DOCUMENTS

| | | |
|---|---|---|
| 6,406,456 B1 | 6/2002 | Slate et al. |
| 6,447,482 B1 | 9/2002 | Roenborg et al. |
| 6,454,743 B1 | 9/2002 | Weber |
| 6,503,454 B1 | 1/2003 | Hadimioglu et al. |
| 6,520,928 B1 | 2/2003 | Junior |
| 6,540,672 B1 | 4/2003 | Simonsen et al. |
| 6,544,234 B1 | 4/2003 | Gabriel |
| 6,547,755 B1 | 4/2003 | Lippe et al. |
| 6,562,006 B1 | 5/2003 | Hjertman et al. |
| 6,569,123 B2 | 5/2003 | Alchas et al. |
| 6,569,127 B1 | 5/2003 | Fago et al. |
| 6,599,272 B1 | 7/2003 | Hjertman et al. |
| 6,641,561 B1 | 11/2003 | Hill et al. |
| 6,645,169 B1 | 11/2003 | Slate et al. |
| 6,645,177 B1 | 11/2003 | Shearn |
| 6,648,858 B2 | 11/2003 | Asbaghi |
| 6,652,483 B2 | 11/2003 | Slate et al. |
| D483,116 S | 12/2003 | Castellano |
| 6,656,163 B1 | 12/2003 | Marshall et al. |
| 6,656,164 B1 | 12/2003 | Smith |
| 6,669,664 B2 | 12/2003 | Slate et al. |
| 6,692,469 B1 | 2/2004 | Weekes et al. |
| 6,743,202 B2 | 6/2004 | Hirschman et al. |
| 6,746,427 B2 | 6/2004 | Duchon et al. |
| 6,752,787 B1 | 6/2004 | Causey et al. |
| 6,767,336 B1 | 7/2004 | Kaplan |
| 6,770,052 B2 | 8/2004 | Hill et al. |
| 6,796,957 B2 | 9/2004 | Carpenter et al. |
| 6,805,686 B1 | 10/2004 | Fathallah et al. |
| 6,808,507 B2 | 10/2004 | Roser |
| 6,817,986 B2 | 11/2004 | Slate et al. |
| 6,835,193 B2 | 12/2004 | Epstein et al. |
| 6,854,620 B2 | 2/2005 | Ramey |
| 6,890,319 B1 | 5/2005 | Crocker |
| 6,932,793 B1 | 8/2005 | Marshall et al. |
| 6,979,316 B1 | 12/2005 | Rubin et al. |
| 6,986,760 B2 | 1/2006 | Giambattista et al. |
| 7,008,399 B2 | 3/2006 | Larsen et al. |
| 7,011,649 B2 | 3/2006 | De et al. |
| 7,025,774 B2 | 4/2006 | Freeman et al. |
| 7,041,085 B2 | 5/2006 | Perez et al. |
| 7,066,909 B1 | 6/2006 | Peter et al. |
| 7,094,230 B2 | 8/2006 | Flaherty et al. |
| 7,097,637 B2 | 8/2006 | Triplett et al. |
| 7,104,400 B2 | 9/2006 | Kiehne |
| 7,118,553 B2 | 10/2006 | Scherer |
| 7,226,450 B2 | 6/2007 | Athanasiou et al. |
| 7,255,684 B2 | 8/2007 | Zubry |
| 7,273,469 B1 | 9/2007 | Chan et al. |
| 7,290,573 B2 | 11/2007 | Py et al. |
| 7,291,132 B2 | 11/2007 | DeRuntz et al. |
| 7,297,135 B2 | 11/2007 | Jeffrey |
| 7,297,136 B2 | 11/2007 | Wyrick |
| 7,357,790 B2 | 4/2008 | Hommann et al. |
| 7,361,160 B2 | 4/2008 | Hommann et al. |
| 7,370,759 B2 | 5/2008 | Hommann |
| 7,381,201 B2 | 6/2008 | Gilbert et al. |
| 7,390,319 B2 | 6/2008 | Friedman |
| 7,442,185 B2 | 10/2008 | Amark et al. |
| 7,449,012 B2 | 11/2008 | Young et al. |
| 7,476,217 B2 | 1/2009 | Martin et al. |
| 7,500,963 B2 | 3/2009 | Westbye et al. |
| 7,500,966 B2 | 3/2009 | Hommann |
| 7,553,294 B2 | 6/2009 | Lazzaro et al. |
| 7,597,685 B2 | 10/2009 | Olson |
| 7,635,348 B2 | 12/2009 | Raven et al. |
| 7,635,350 B2 | 12/2009 | Scherer |
| 7,648,483 B2 | 1/2010 | Edwards et al. |
| 7,654,987 B2 | 2/2010 | Hommann et al. |
| 7,670,314 B2 | 3/2010 | Wall et al. |
| 7,686,789 B2 | 3/2010 | Nemoto et al. |
| 7,731,686 B2 | 6/2010 | Edwards et al. |
| D619,706 S | 7/2010 | Schon et al. |
| 7,749,195 B2 | 7/2010 | Hommann |
| 7,760,099 B2 | 7/2010 | Knight |
| 7,785,292 B2 | 8/2010 | Harrison |
| D625,015 S | 10/2010 | Hansen et al. |
| 7,828,776 B2 | 11/2010 | Nemoto et al. |
| D628,690 S | 12/2010 | Galbraith |
| 7,857,791 B2 | 12/2010 | Jacobs et al. |
| 7,887,513 B2 | 2/2011 | Nemoto et al. |
| 7,901,377 B1 | 3/2011 | Harrison et al. |
| 7,909,796 B2 | 3/2011 | Weber |
| 7,918,823 B2 | 4/2011 | Edwards et al. |
| 7,922,695 B2 | 4/2011 | Wiegel et al. |
| D637,713 S | 5/2011 | Nord et al. |
| 7,938,803 B2 | 5/2011 | Mernoe et al. |
| D642,261 S | 7/2011 | York et al. |
| 7,976,499 B2 | 7/2011 | Grunhut et al. |
| 8,012,120 B2 | 9/2011 | Slate et al. |
| 8,012,125 B1 | 9/2011 | Fago et al. |
| 8,016,797 B2 | 9/2011 | Gratwohl et al. |
| 8,043,262 B2 | 10/2011 | Streit et al. |
| 8,048,037 B2 | 11/2011 | Kohlbrenner et al. |
| 8,052,645 B2 * | 11/2011 | Slate ................... A61M 5/20 604/154 |
| D650,070 S | 12/2011 | Mori |
| 8,088,096 B2 | 1/2012 | Lauchard et al. |
| 8,105,271 B2 | 1/2012 | Matusch |
| 8,141,417 B2 | 3/2012 | Gibson et al. |
| 8,152,779 B2 | 4/2012 | Cabiri |
| 8,177,749 B2 * | 5/2012 | Slate ................... A61M 5/20 604/131 |
| 8,221,356 B2 | 7/2012 | Enggaard et al. |
| 8,226,610 B2 | 7/2012 | Edwards et al. |
| 8,277,414 B2 | 10/2012 | Barrow-Williams et al. |
| 8,298,171 B2 | 10/2012 | Ishikawa et al. |
| 8,308,687 B2 | 11/2012 | Carrel et al. |
| 8,337,472 B2 | 12/2012 | Edginton et al. |
| D673,677 S | 1/2013 | Noda et al. |
| 8,343,103 B2 | 1/2013 | Moser |
| 8,376,985 B2 | 2/2013 | Pongpairochana et al. |
| D679,008 S | 3/2013 | Schroeder et al. |
| D679,391 S | 4/2013 | Chinowsky et al. |
| 8,491,538 B2 | 7/2013 | Kohlbrenner et al. |
| 8,523,803 B1 | 9/2013 | Favreau |
| 8,591,465 B2 | 11/2013 | Hommann |
| D694,879 S | 12/2013 | Julian et al. |
| 8,603,026 B2 | 12/2013 | Favreau |
| 8,603,027 B2 | 12/2013 | Favreau |
| 8,609,621 B2 | 12/2013 | Bedzyk et al. |
| 8,628,723 B2 | 1/2014 | Vandergaw |
| D702,343 S | 4/2014 | Dale et al. |
| D702,835 S | 4/2014 | Vinchon |
| 8,690,827 B2 | 4/2014 | Edwards et al. |
| 8,696,628 B2 | 4/2014 | Grunhut |
| 8,716,711 B2 | 5/2014 | Iwasaki |
| D718,439 S | 11/2014 | Woehr et al. |
| 8,900,204 B2 | 12/2014 | Geertsen |
| 8,911,410 B2 | 12/2014 | Ekman et al. |
| 8,960,827 B2 | 2/2015 | McMillin et al. |
| 8,961,473 B2 | 2/2015 | Heald |
| 8,968,255 B2 | 3/2015 | Oakland |
| 9,011,386 B2 | 4/2015 | Kronestedt et al. |
| 9,138,542 B2 | 9/2015 | Smith |
| D748,783 S | 2/2016 | Zhang et al. |
| 9,278,177 B2 | 3/2016 | Edwards et al. |
| D757,254 S | 5/2016 | Wohlfahrt et al. |
| D765,241 S | 8/2016 | Holland |
| D768,851 S | 10/2016 | Rozwadowski et al. |
| D768,852 S | 10/2016 | Rozwadowski et al. |
| 9,616,173 B2 | 4/2017 | Slate et al. |
| 9,649,443 B2 | 5/2017 | Klintenstedt et al. |
| 9,925,336 B2 * | 3/2018 | Slate ................... A61M 5/20 |
| 9,974,904 B2 | 5/2018 | Burk et al. |
| 10,092,703 B2 | 10/2018 | Mounce et al. |
| 10,092,706 B2 | 10/2018 | Denzer et al. |
| 10,492,990 B2 | 12/2019 | Mounce et al. |
| 10,639,422 B2 * | 5/2020 | Slate ................... A61M 5/326 |
| D898,908 S | 10/2020 | Denzer et al. |
| 11,020,537 B2 | 6/2021 | Mounce et al. |
| 2001/0005781 A1 | 6/2001 | Bergens et al. |
| 2001/0011163 A1 | 8/2001 | Nolan et al. |
| 2001/0018548 A1 | 8/2001 | Silverman et al. |

(56) References Cited

U.S. PATENT DOCUMENTS

| | | |
|---|---|---|
| 2001/0018937 A1 | 9/2001 | Nemoto |
| 2001/0034502 A1 | 10/2001 | Moberg et al. |
| 2001/0047153 A1 | 11/2001 | Trocki et al. |
| 2002/0016569 A1 | 2/2002 | Critchlow et al. |
| 2002/0022066 A1 | 2/2002 | Matsubayashi et al. |
| 2002/0029018 A1 | 3/2002 | Jeffrey |
| 2002/0045864 A1 | 4/2002 | Perez et al. |
| 2002/0095120 A1 | 7/2002 | Larsen et al. |
| 2002/0099334 A1 | 7/2002 | Hanson et al. |
| 2002/0133113 A1 | 9/2002 | Madsen et al. |
| 2002/0133114 A1 | 9/2002 | Itoh et al. |
| 2002/0151855 A1 | 10/2002 | Douglas et al. |
| 2002/0156426 A1 | 10/2002 | Gagnieux et al. |
| 2003/0036725 A1 | 2/2003 | Lavi et al. |
| 2003/0050592 A1 | 3/2003 | Slate et al. |
| 2003/0065536 A1 | 4/2003 | Hansen et al. |
| 2003/0105430 A1 | 6/2003 | Lavi et al. |
| 2003/0114798 A1 | 6/2003 | Langley et al. |
| 2003/0233070 A1 | 12/2003 | De La Serna et al. |
| 2003/0236502 A1 | 12/2003 | De et al. |
| 2004/0019326 A1 | 1/2004 | Gilbert et al. |
| 2004/0039336 A1 | 2/2004 | Amark et al. |
| 2004/0054327 A1 | 3/2004 | Gillespie |
| 2004/0068266 A1 | 4/2004 | Delmotte |
| 2004/0116861 A1 | 6/2004 | Trocki et al. |
| 2004/0129803 A1 | 7/2004 | Dolder et al. |
| 2004/0133154 A1 | 7/2004 | Flaherty et al. |
| 2004/0133162 A1 | 7/2004 | Trocki et al. |
| 2004/0153008 A1 | 8/2004 | Sharf et al. |
| 2004/0208845 A1 | 10/2004 | Michal et al. |
| 2004/0225262 A1 | 11/2004 | Fathallah et al. |
| 2004/0258756 A1 | 12/2004 | McLoughlin |
| 2005/0020979 A1 | 1/2005 | Westbye et al. |
| 2005/0027255 A1 | 2/2005 | Lavi et al. |
| 2005/0033242 A1 | 2/2005 | Perez et al. |
| 2005/0049561 A1 | 3/2005 | Hommann et al. |
| 2005/0054987 A1 | 3/2005 | Perez et al. |
| 2005/0080377 A1 | 4/2005 | Sadowski et al. |
| 2005/0148869 A1 | 7/2005 | Masuda |
| 2005/0165404 A1 | 7/2005 | Miller |
| 2005/0171476 A1 | 8/2005 | Judson et al. |
| 2005/0171477 A1 | 8/2005 | Rubin et al. |
| 2005/0197650 A1 | 9/2005 | Sugimoto et al. |
| 2005/0203466 A1 | 9/2005 | Hommann et al. |
| 2005/0209569 A1 | 9/2005 | Ishikawa et al. |
| 2005/0261633 A1 | 11/2005 | Khalaj |
| 2005/0261693 A1 | 11/2005 | Miller et al. |
| 2005/0277885 A1 | 12/2005 | Scherer |
| 2006/0022363 A1 | 2/2006 | Konno et al. |
| 2006/0030819 A1 | 2/2006 | Young et al. |
| 2006/0157064 A1 | 7/2006 | Davison et al. |
| 2006/0173408 A1 | 8/2006 | Wyrick |
| 2006/0251646 A1 | 11/2006 | Utku |
| 2006/0258990 A1 | 11/2006 | Weber |
| 2006/0270985 A1 | 11/2006 | Hommann et al. |
| 2007/0021720 A1 | 1/2007 | Guillermo |
| 2007/0025879 A1 | 2/2007 | Vandergaw |
| 2007/0027430 A1 | 2/2007 | Hommann |
| 2007/0066938 A1 | 3/2007 | Iio et al. |
| 2007/0100281 A1 | 5/2007 | Morris et al. |
| 2007/0112301 A1 | 5/2007 | Preuthun et al. |
| 2007/0112310 A1 | 5/2007 | Lavi et al. |
| 2007/0118081 A1 | 5/2007 | Daily et al. |
| 2007/0135767 A1 | 6/2007 | Gillespie et al. |
| 2007/0142787 A1 | 6/2007 | Scherer |
| 2007/0149925 A1 | 6/2007 | Edwards et al. |
| 2007/0167920 A1 | 7/2007 | Hommann |
| 2007/0173770 A1 | 7/2007 | Stamp |
| 2007/0197954 A1 | 8/2007 | Keenan |
| 2007/0197968 A1* | 8/2007 | Pongpairochana ..... A61M 5/34 604/67 |
| 2007/0219498 A1 | 9/2007 | Malone et al. |
| 2007/0233001 A1 | 10/2007 | Burroughs et al. |
| 2007/0239114 A1 | 10/2007 | Edwards et al. |
| 2007/0250010 A1 | 10/2007 | Hohlfelder et al. |
| 2007/0265568 A1 | 11/2007 | Tsals et al. |
| 2008/0015510 A1 | 1/2008 | Sandoz et al. |
| 2008/0039795 A1 | 2/2008 | Slate et al. |
| 2008/0051711 A1 | 2/2008 | Mounce et al. |
| 2008/0051714 A1 | 2/2008 | Moberg et al. |
| 2008/0051715 A1 | 2/2008 | Young et al. |
| 2008/0097325 A1 | 4/2008 | Tanaka et al. |
| 2008/0132841 A1 | 6/2008 | Chiwanga et al. |
| 2008/0140007 A1 | 6/2008 | Glynn |
| 2008/0262423 A1 | 10/2008 | Ingram et al. |
| 2008/0262434 A1 | 10/2008 | Vaillancourt |
| 2008/0312602 A1 | 12/2008 | Barrow-Williams et al. |
| 2009/0018494 A1 | 1/2009 | Nemoto et al. |
| 2009/0018505 A1 | 1/2009 | Arguedas et al. |
| 2009/0024112 A1 | 1/2009 | Edwards et al. |
| 2009/0043253 A1 | 2/2009 | Podaima |
| 2009/0076383 A1 | 3/2009 | Toews et al. |
| 2009/0149744 A1 | 6/2009 | Nemoto et al. |
| 2009/0254060 A1 | 10/2009 | Hetherington |
| 2009/0270672 A1 | 10/2009 | Fago |
| 2009/0281505 A1 | 11/2009 | Hansen et al. |
| 2009/0292246 A1 | 11/2009 | Slate et al. |
| 2009/0299288 A1 | 12/2009 | Sie et al. |
| 2009/0299290 A1 | 12/2009 | Moberg |
| 2009/0312705 A1 | 12/2009 | Grunhut et al. |
| 2009/0322545 A1 | 12/2009 | Gibson et al. |
| 2009/0326459 A1 | 12/2009 | Shipway et al. |
| 2010/0016793 A1 | 1/2010 | Jennings et al. |
| 2010/0016795 A1 | 1/2010 | McLoughlin |
| 2010/0021456 A1 | 1/2010 | Miossec et al. |
| 2010/0022955 A1 | 1/2010 | Slate et al. |
| 2010/0036318 A1 | 2/2010 | Raday et al. |
| 2010/0036320 A1 | 2/2010 | Cox et al. |
| 2010/0042054 A1 | 2/2010 | Elahi et al. |
| 2010/0112679 A1 | 5/2010 | Vandergaw |
| 2010/0152655 A1 | 6/2010 | Stamp |
| 2010/0152659 A1 | 6/2010 | Streit et al. |
| 2010/0160894 A1 | 6/2010 | Julian et al. |
| 2010/0185152 A1 | 7/2010 | Larsen et al. |
| 2010/0198060 A1 | 8/2010 | Fago et al. |
| 2010/0268170 A1 | 10/2010 | Carrel et al. |
| 2010/0312195 A1 | 12/2010 | Johansen et al. |
| 2011/0004165 A1 | 1/2011 | Iio et al. |
| 2011/0023281 A1 | 2/2011 | Schraga |
| 2011/0044998 A1 | 2/2011 | Bedian et al. |
| 2011/0047153 A1 | 2/2011 | Betz |
| 2011/0092915 A1 | 4/2011 | Olson et al. |
| 2011/0097229 A1 | 4/2011 | Cauley et al. |
| 2011/0098655 A1 | 4/2011 | Jennings et al. |
| 2011/0137286 A1 | 6/2011 | Mudd et al. |
| 2011/0144594 A1 | 6/2011 | Sund et al. |
| 2011/0152781 A1 | 6/2011 | Brunnberg et al. |
| 2011/0160580 A1 | 6/2011 | Perkins et al. |
| 2011/0166512 A1 | 7/2011 | Both et al. |
| 2011/0184383 A1 | 7/2011 | Hasegawa |
| 2011/0190693 A1 | 8/2011 | Takatsuka et al. |
| 2011/0190702 A1 | 8/2011 | Stumber |
| 2011/0196339 A1 | 8/2011 | Hirschel et al. |
| 2011/0202011 A1 | 8/2011 | Wozencroft |
| 2011/0213315 A1 | 9/2011 | Sweeney et al. |
| 2011/0224616 A1 | 9/2011 | Slate et al. |
| 2011/0224620 A1 | 9/2011 | Johansen et al. |
| 2011/0224621 A1 | 9/2011 | Johansen et al. |
| 2011/0230833 A1 | 9/2011 | Landman et al. |
| 2011/0245761 A1 | 10/2011 | Jennings et al. |
| 2011/0257596 A1 | 10/2011 | Gaudet |
| 2011/0257604 A1 | 10/2011 | Banik |
| 2011/0264046 A1 | 10/2011 | Nyholm et al. |
| 2011/0270220 A1 | 11/2011 | Genosar |
| 2012/0035472 A1 | 2/2012 | Bruce et al. |
| 2012/0035538 A1 | 2/2012 | Elmen et al. |
| 2012/0056019 A1 | 3/2012 | Renz et al. |
| 2012/0059319 A1 | 3/2012 | Segal |
| 2012/0089119 A1 | 4/2012 | Slate et al. |
| 2012/0101439 A9 | 4/2012 | Slate et al. |
| 2012/0172815 A1 | 7/2012 | Holmqvist |
| 2012/0238961 A1 | 9/2012 | Julian et al. |
| 2012/0253314 A1 | 10/2012 | Harish et al. |
| 2012/0265142 A1 | 10/2012 | Slate et al. |

(56) References Cited

U.S. PATENT DOCUMENTS

| | | |
|---|---|---|
| 2012/0296286 A1 | 11/2012 | Raab et al. |
| 2012/0323176 A1 | 12/2012 | Watanabe et al. |
| 2013/0018313 A1 | 1/2013 | Kramer et al. |
| 2013/0018315 A1 | 1/2013 | Blomquist |
| 2013/0030383 A1 | 1/2013 | Keitel |
| 2013/0035647 A1 | 2/2013 | Veasey et al. |
| 2013/0046248 A1 | 2/2013 | Raab |
| 2013/0110049 A1 | 5/2013 | Cronenberg et al. |
| 2013/0110054 A1 | 5/2013 | Raab et al. |
| 2013/0112521 A1 | 5/2013 | Ekman et al. |
| 2013/0131595 A1 | 5/2013 | Ekman et al. |
| 2013/0131601 A1 | 5/2013 | Pommereau et al. |
| 2013/0190719 A1 | 7/2013 | Smith et al. |
| 2013/0190721 A1 | 7/2013 | Kemp et al. |
| 2013/0204198 A1 | 8/2013 | Burnell et al. |
| 2013/0204204 A1 | 8/2013 | Butler et al. |
| 2013/0218092 A1 | 8/2013 | Davies et al. |
| 2013/0226091 A1 | 8/2013 | Nzike et al. |
| 2013/0261558 A1 | 10/2013 | Hourmand et al. |
| 2013/0274668 A1 | 10/2013 | Barrow-Williams et al. |
| 2013/0281936 A1 | 10/2013 | Kemp et al. |
| 2013/0289491 A1 | 10/2013 | Kramer et al. |
| 2013/0310744 A1 | 11/2013 | Brereton et al. |
| 2013/0310761 A1 | 11/2013 | Plumptre |
| 2013/0317430 A1 | 11/2013 | Brereton et al. |
| 2013/0317480 A1 | 11/2013 | Reber et al. |
| 2013/0324935 A1 | 12/2013 | Brereton et al. |
| 2013/0338601 A1 | 12/2013 | Cowe |
| 2014/0046259 A1 | 2/2014 | Reber et al. |
| 2014/0148784 A1 | 5/2014 | Anderson et al. |
| 2014/0194854 A1 | 7/2014 | Tsals |
| 2014/0236087 A1 | 8/2014 | Alderete et al. |
| 2014/0257197 A1 | 9/2014 | Madsen et al. |
| 2014/0276448 A1 | 9/2014 | Muller-Pathle et al. |
| 2014/0296825 A1 | 10/2014 | Lemaire et al. |
| 2014/0303556 A1 | 10/2014 | Travanty |
| 2014/0316369 A1 | 10/2014 | Centeno et al. |
| 2014/0330203 A1 | 11/2014 | McLoughlin et al. |
| 2014/0330216 A1 | 11/2014 | Weaver et al. |
| 2014/0336590 A1 | 11/2014 | Hourmand et al. |
| 2014/0364808 A1 | 12/2014 | Niklaus et al. |
| 2015/0045729 A1 | 2/2015 | Denzer et al. |
| 2015/0080809 A1 | 3/2015 | Dasbach et al. |
| 2015/0136809 A1 | 5/2015 | Hamann et al. |
| 2015/0141923 A1 | 5/2015 | Wurmbauer et al. |
| 2015/0151046 A1 | 6/2015 | Nagel et al. |
| 2015/0165130 A1 | 6/2015 | Butler et al. |
| 2015/0217057 A1 | 8/2015 | Hogdahl |
| 2016/0022914 A1 | 1/2016 | Mounce et al. |
| 2016/0120751 A1 | 5/2016 | Mounce et al. |
| 2016/0271326 A1 | 9/2016 | Slate et al. |
| 2017/0043105 A1 | 2/2017 | Elmen |
| 2017/0157326 A1 | 6/2017 | Slate et al. |

FOREIGN PATENT DOCUMENTS

| | | |
|---|---|---|
| CA | 2594627 A1 | 8/2006 |
| DE | 102007061775 A1 | 7/2009 |
| EP | 0654279 A2 | 5/1995 |
| EP | 1219312 A2 | 7/2002 |
| EP | 1227423 A1 | 7/2002 |
| EP | 1518575 A1 | 3/2005 |
| EP | 1859827 A1 | 11/2007 |
| EP | 0620748 B1 | 7/2010 |
| EP | 2654832 A1 | 10/2013 |
| ES | 2121536 A1 | 11/1998 |
| FR | 2390175 A2 | 12/1978 |
| FR | 2581548 A1 | 11/1986 |
| FR | 2592307 A1 | 7/1987 |
| FR | 2622457 A1 | 5/1989 |
| FR | 2716375 A1 | 8/1995 |
| IL | 87559 A | 6/1993 |
| IL | 877559 | 6/1993 |
| JP | 63-139563 A | 6/1988 |
| JP | 02-008157 A | 1/1990 |
| JP | 07-503384 A | 4/1995 |
| JP | 07-184938 A | 7/1995 |
| JP | 07-185000 A | 7/1995 |
| JP | 11-276583 A | 10/1999 |
| JP | 2000-237309 A | 9/2000 |
| JP | 2001-518366 A | 10/2001 |
| JP | 2002-531228 A | 9/2002 |
| JP | 2002-333851 A | 11/2002 |
| JP | 2002-543931 A | 12/2002 |
| JP | 2003-180828 A | 7/2003 |
| JP | 2003-220142 A | 8/2003 |
| JP | 2005-131007 A | 5/2005 |
| JP | 2005-514082 A | 5/2005 |
| JP | 2005-287676 A | 10/2005 |
| JP | 2005-530565 | 10/2005 |
| JP | 2006-507061 A | 3/2006 |
| JP | 2006-230701 A | 9/2006 |
| JP | 2006-523507 A | 10/2006 |
| JP | 2006-528040 A | 12/2006 |
| JP | 2007-500561 A | 1/2007 |
| JP | 2007-507260 A | 3/2007 |
| JP | 2007-111518 A | 5/2007 |
| JP | 2007-127086 A | 5/2007 |
| JP | 2007-522853 A | 8/2007 |
| JP | 2007-529243 A | 10/2007 |
| JP | 2008-508961 A | 3/2008 |
| JP | 2009-511177 A | 3/2009 |
| JP | 2010-051828 A | 3/2010 |
| JP | 2010-511414 A | 4/2010 |
| JP | 2015-186876 A | 10/2015 |
| JP | 6038884 B2 | 12/2016 |
| JP | 2017-023813 A | 2/2017 |
| TW | 200833383 A | 8/2008 |
| TW | 200833387 A | 8/2008 |
| TW | 200836787 A | 9/2008 |
| TW | 200840606 A | 10/2008 |
| TW | 201004667 A | 2/2010 |
| TW | 201004668 A | 2/2010 |
| WO | 86/06967 A1 | 12/1986 |
| WO | 87/03494 A1 | 6/1987 |
| WO | 87/07160 A1 | 12/1987 |
| WO | 91/18634 A1 | 12/1991 |
| WO | 92/06725 A1 | 4/1992 |
| WO | 92/08506 A1 | 5/1992 |
| WO | 92/21392 A1 | 12/1992 |
| WO | 93/02728 A1 | 2/1993 |
| WO | 93/13817 A1 | 7/1993 |
| WO | 93/24160 A1 | 12/1993 |
| WO | 93/25256 A1 | 12/1993 |
| WO | 94/06494 A1 | 3/1994 |
| WO | 94/07553 A1 | 4/1994 |
| WO | 95/21645 A1 | 8/1995 |
| WO | 95/25555 A1 | 9/1995 |
| WO | 95/31235 A1 | 11/1995 |
| WO | 95/34333 A2 | 12/1995 |
| WO | 96/00594 A1 | 1/1996 |
| WO | 96/21482 A2 | 7/1996 |
| WO | 96/26754 A2 | 9/1996 |
| WO | 96/38190 A1 | 12/1996 |
| WO | 97/07839 A1 | 3/1997 |
| WO | 97/31665 A1 | 9/1997 |
| WO | 98/13077 A2 | 4/1998 |
| WO | 98/17332 A2 | 4/1998 |
| WO | 98/21408 A1 | 5/1998 |
| WO | 98/28032 A1 | 7/1998 |
| WO | 99/17823 A1 | 4/1999 |
| WO | 99/20327 A2 | 4/1999 |
| WO | 99/21600 A2 | 5/1999 |
| WO | 99/65548 A1 | 12/1999 |
| WO | 00/02605 A1 | 1/2000 |
| WO | 00/09186 A2 | 2/2000 |
| WO | 00/24441 A1 | 5/2000 |
| WO | 00/25846 A2 | 5/2000 |
| WO | 01/00261 A1 | 1/2001 |
| WO | 01/37903 A2 | 5/2001 |
| WO | 01/41835 A2 | 6/2001 |
| WO | 01/89634 A2 | 11/2001 |
| WO | 02/07812 A2 | 1/2002 |
| WO | 02/11792 A1 | 2/2002 |

(56) References Cited

FOREIGN PATENT DOCUMENTS

| | | |
|---|---|---|
| WO | 02/49691 A2 | 6/2002 |
| WO | 02/60513 A2 | 8/2002 |
| WO | 02/92153 A2 | 11/2002 |
| WO | 03/03934 A1 | 1/2003 |
| WO | 03/06099 A1 | 1/2003 |
| WO | 03/08023 A1 | 1/2003 |
| WO | 03/24385 A1 | 3/2003 |
| WO | 03/39634 A1 | 5/2003 |
| WO | 03/47659 A1 | 6/2003 |
| WO | 03/47663 A2 | 6/2003 |
| WO | 03/90509 A2 | 11/2003 |
| WO | 2003/103749 A2 | 12/2003 |
| WO | 2004/000395 A1 | 12/2003 |
| WO | 2004/004809 A1 | 1/2004 |
| WO | 2004/004825 A2 | 1/2004 |
| WO | 2004/069303 A2 | 8/2004 |
| WO | 2004/084795 A1 | 10/2004 |
| WO | 2004/108193 A1 | 12/2004 |
| WO | 2005/032449 A1 | 4/2005 |
| WO | 2005/053771 A2 | 6/2005 |
| WO | 2005/070481 A1 | 8/2005 |
| WO | 2005/077441 A2 | 8/2005 |
| WO | 2005/079440 A2 | 9/2005 |
| WO | 2005/089831 A1 | 9/2005 |
| WO | 2005/094923 A1 | 10/2005 |
| WO | 2006/015501 A1 | 2/2006 |
| WO | 2006/017732 A2 | 2/2006 |
| WO | 2006/020609 A1 | 2/2006 |
| WO | 2006/062788 A2 | 6/2006 |
| WO | 2006/063015 A2 | 6/2006 |
| WO | 2006/084821 A2 | 8/2006 |
| WO | 2006/086774 A2 | 8/2006 |
| WO | 2007/002053 A2 | 1/2007 |
| WO | 2007/044980 A2 | 4/2007 |
| WO | 2007/047200 A1 | 4/2007 |
| WO | 2007/053779 A2 | 5/2007 |
| WO | 2007/075677 A2 | 7/2007 |
| WO | 2007/099044 A1 | 9/2007 |
| WO | 2007/126851 A2 | 11/2007 |
| WO | 2007/138299 A1 | 12/2007 |
| WO | 2007/138313 A1 | 12/2007 |
| WO | 2007/140610 A1 | 12/2007 |
| WO | 2008/004670 A1 | 1/2008 |
| WO | 2008/021776 A2 | 2/2008 |
| WO | 2008/024810 A2 | 2/2008 |
| WO | 2008/048750 A2 | 4/2008 |
| WO | 2008/064092 A2 | 5/2008 |
| WO | 2008/075033 A1 | 6/2008 |
| WO | 2008/083313 A2 | 7/2008 |
| WO | 2008/093063 A2 | 8/2008 |
| WO | 2008/094984 A2 | 8/2008 |
| WO | 2008/095124 A1 | 8/2008 |
| WO | 2008/107670 A2 | 9/2008 |
| WO | 2008/113772 A1 | 9/2008 |
| WO | 2008/139458 A2 | 11/2008 |
| WO | 2008/139460 A2 | 11/2008 |
| WO | 2008/146021 A1 | 12/2008 |
| WO | 2009/006725 A1 | 1/2009 |
| WO | 2009/019437 A1 | 2/2009 |
| WO | 2009/097325 A1 | 8/2009 |
| WO | 2009/125879 A1 | 10/2009 |
| WO | 2009/143255 A1 | 11/2009 |
| WO | 2010/023481 A1 | 3/2010 |
| WO | 2010/026414 A1 | 3/2010 |
| WO | 2010/076275 A1 | 7/2010 |
| WO | 2010/089313 A1 | 8/2010 |
| WO | 2010/091133 A2 | 8/2010 |
| WO | 2010/099850 A1 | 9/2010 |
| WO | 2010/100213 A1 | 9/2010 |
| WO | 2010/127449 A1 | 11/2010 |
| WO | 2011/014525 A2 | 2/2011 |
| WO | 2011/056888 A2 | 5/2011 |
| WO | 2011/057065 A1 | 5/2011 |
| WO | 2011/089206 A2 | 7/2011 |
| WO | 2012/000871 A1 | 1/2012 |
| WO | 2012/000940 A2 | 1/2012 |
| WO | 2012/022771 A2 | 2/2012 |
| WO | 2012/080481 A1 | 6/2012 |
| WO | 2012/103140 A1 | 8/2012 |
| WO | 2012/145685 A1 | 10/2012 |
| WO | 2012/164389 A2 | 12/2012 |
| WO | 2012/164394 A2 | 12/2012 |
| WO | 2012/164397 A1 | 12/2012 |
| WO | 2013/001378 A2 | 1/2013 |
| WO | 2013/034984 A2 | 3/2013 |
| WO | 2013/034986 A2 | 3/2013 |
| WO | 2013/065055 A1 | 5/2013 |
| WO | 2014/143815 A2 | 9/2014 |
| WO | 2014/144096 A1 | 9/2014 |

OTHER PUBLICATIONS

Taiwan Patent Application No. 107100925, Search Report, dated Sep. 7, 2018.
U.S. Appl. No. 17/003,665, Notice of Allowance, mailed Sep. 20, 2023.
U.S. Appl. No. 17/147,659, Final Office Action, mailed Oct. 4, 2023.
U.S. Appl. No. 17/147,659, Non-Final Office Action, mailed Jun. 23, 2023.
U.S. Appl. No. 17/147,659, Requirement for Restriction/Election, mailed Apr. 12, 2023.
U.S. Appl. No. 17/241,329, Advisory Action, mailed Jul. 10, 2023.
U.S. Appl. No. 17/241,329, Final Office Action, mailed Apr. 14, 2023.
U.S. Appl. No. 17/241,329, Non-Final Office Action, mailed Aug. 11, 2023.
U.S. Appl. No. 17/241,329, Non-Final Office Action, mailed Nov. 25, 2022.
U.S. Appl. No. 14/777,255, Nonfinal Office Action, dated Aug. 27, 2018.
U.S. Appl. No. 14/777,255, Nonfinal Office Action, dated Mar. 7, 2019.
U.S. Appl. No. 14/777,255, Notice of Allowance, dated Jul. 29, 2019.
U.S. Appl. No. 15/782,925, Nonfinal Office Action, dated Mar. 11, 2019.
U.S. Appl. No. 15/782,951, Final Office Action, dated Aug. 1, 2019.
U.S. Appl. No. 15/782,951, Nonfinal Office Action, dated Mar. 11, 2019.
Australian Patent Application No. 2009249027, Notice of Acceptance, dated Aug. 7, 2014.
Australian Patent Application No. 2009249027, Office Action, mailed Jul. 24, 2013.
Australian Patent Application No. 2012245231, Notice of Allowance, mailed Oct. 4, 2016.
Australian Patent Application No. 2012245231, Office Action, mailed Jul. 5, 2016.
Australian Patent Application No. 2012245231, Office Action, mailed Oct. 19, 2015.
Australian Patent Application No. 2014268139, Office Action, mailed Jul. 19, 2016.
Australian Patent Application No. 2014268140, Office Action, mailed Jul. 22, 2016.
Australian Patent Application No. 2014268140, Office Action, mailed Sep. 2, 2016.
Australian Patent Application No. 2017200125, Office Action, mailed Sep. 18, 2017.
Australian Patent Application No. 2017202210, Office Action, mailed Oct. 25, 2018.
Australian Patent Application No. 2018253467, Office Action, mailed Dec. 6, 2019.
Australian Patent Application No. 2019202863, Office Action, mailed Sep. 13, 2019.
CA Patent Application No. 3070644, Examination Report, mailed Aug. 16, 2021.
Canadian Patent Application No. 2724641, Office Action, mailed Dec. 15, 2016.

(56) References Cited

OTHER PUBLICATIONS

Canadian Patent Application No. 2724641, Office Action, mailed Jun. 4, 2015.
Canadian Patent Application No. 2724641, Office Action, mailed May 27, 2019.
Canadian patent application No. 2724641, Office Action, mailed Sep. 29, 2017.
Canadian patent application No. 2833748, Examination Report, dated Aug. 12, 2016.
Canadian Patent Application No. 2833748, Office Action, mailed May 2, 2017.
Canadian Patent Application No. 2833748, Office Action, mailed Nov. 23, 2015.
Canadian Patent Application No. 3021845, Office Action, dated Dec. 4, 2020.
Canadian Patent Application No. 3021845, Office Action, mailed Aug. 19, 2019.
Canadian Patent Application No. 3021845, Office Action, mailed May 7, 2020.
European Application No. 22177279.1, European Search Report and Opinion, mailed Sep. 19, 2022.
European patent application No. 09751483.0, Extended Search Report, dated Aug. 1, 2013.
European Patent Application No. 09751483.0, Office Action, dated Apr. 10, 2015.
European Patent Application No. 09751483.0, Office Action, dated Nov. 16, 2015.
European patent Application No. 09751483.0, Office Action, mailed Aug. 1, 2016.
European Patent Application No. 09751483.0, Office Action, mailed May 14, 2014.
European Patent Application No. 12774589.1, Extended Search Report, dated Jul. 8, 2015.
European patent application No. 12774589.1, Extended Search Report, mailed Feb. 23, 2015.
European Patent Application No. 12774589.1, Office Action, mailed Oct. 31, 2017.
European Patent Application No. 14763010.7, Extended Search Report and Opinion, mailed Jan. 10, 2017.
European patent application No. 14763010.7, Partial Supplementary Search Report, mailed Oct. 24, 2016.
European patent application No. 14765760.5, Extended Search Report, dated Jan. 11, 2017.
European Patent Application No. 14765760.5, Office Action, mailed Jul. 9, 2019.
European patent application No. 14765760.5, Partial Supplementary Search Report, mailed Oct. 24, 2016.
European Patent Application No. 19154409, Decision to grant a European patent, dated Jun. 17, 2022.
European Patent Application No. 19154409.7, European Search Report and Search Opinion, mailed Oct. 31, 2019.
European Patent Application No. 19191313.6, European Search Report, mailed Dec. 16, 2019.
Examiner initiated interview summary, U.S. Appl. No. 15/782,951, Oct. 11, 2019, 2 pages.
Final Office Action, U.S. Appl. No. 15/782,925, filed Oct. 11, 2019.
International Patent Application No. PCT/US2009/044693, International Search Report, mailed Jul. 21, 2009.
International Patent Application No. PCT/US2009/044693, Written Opinion of the International Searchina Authority, mailed May 20, 2009.
International Patent Application No. PCT/US2012/34535, International Search Report and Written Opinion, dated Aug. 17, 2012.
International Patent Application No. PCT/US2014/027950, International Search Report and Written Opinion, dated Oct. 7, 2014.
International Preliminary Report on Patentability for corresponding International Application No. PCT/US2009/044693, Nov. 23, 2010.
International Preliminary Report on Patentability for corresponding International Application No. PCT/US2012/034535, Oct. 22, 2013.
International Preliminary Report on Patentability for corresponding International Application No. PCT/US2014/027950, Sep. 15, 2015.
International Preliminary Report on Patentability for corresponding International Application No. PCT/US2014/028363, Sep. 15, 2015.
International Search Report and Written Opinion, dated Aug. 18, 2014, issued in related international application No. PCT/US2014/028363.
Japanese Application No. 2020-041954 Notice of Reasons for Rejection mailed Jan. 4, 2021.
Japanese Application No. 2021-078657, Notice of Reasons for Rejection, mailed Jan. 16, 2023.
Japanese Patent Application No. 2011-510683, Final Office Action, mailed Jun. 1, 2015.
Japanese Patent Application No. 2011-510683, Notice of Allowance, dated Oct. 5, 2015.
Japanese Patent Application No. 2011-510683, Office Action, mailed Jul. 30, 2013.
Japanese Patent Application No. 2011-510683, Office Action, mailed Jun. 30, 2014.
Japanese Patent Application No. 2014-021052, Final Office Action, mailed Apr. 20, 2015.
Japanese Patent Application No. 2014-506591, Notice of Allowance, mailed Oct. 3, 2016.
Japanese Patent Application No. 2014-506591, Office Action, mailed Jan. 4, 2016.
Japanese Patent Application No. 2015-171851, Office Action, mailed Feb. 6, 2017.
Japanese Patent Application No. 2015-186876, Office Action, mailed Jul. 15, 2016.
Japanese Patent Application No. 2016-214237, Notice of Reasons for Rejection, mailed Sep. 4, 2017.
Japanese Patent Application No. 2016-502669, Notice of Reasons for Rejection, mailed Jan. 14, 2020.
Japanese Patent Application No. 2017-089529, Notice of Reasons for Rejection, mailed Apr. 2, 2018.
Japanese Patent Application No. 2017-089529, Notice of Reasons for Rejection, mailed Sep. 14, 2018.
Japanese Patent Application No. 2018-086731, Decision of Rejection, mailed Feb. 3, 2020.
Japanese Patent Application No. 2018-188224, Notice of Reasons for Rejection, mailed Aug. 5, 2019.
Japanese Patent Application No. 2018-228060, Notice of Reasons for Rejection, Oct. 21, 2019.
Japanese Patent Application No. 2019-070580, Notice of Reasons for Rejection, mailed Feb. 25, 2020.
Japanese Patent Application No. 2020-041954, Decision of Rejection, mailed Aug. 2, 2021.
Japanese Patent Application No. 2020-041954, Office Action, dated Jun. 20, 2022.
Japanese Patent Application No. 2021-078657, Office Action, dated Jun. 6, 2022.
Michael Denzer et al., related copending U.S. Appl. No. 14/112,479, 371(c) dated Sep. 17, 2014.
Notice of Allowance issued in related U.S. Appl. No. 13/454,531, filed Apr. 3, 2014.
Notice of Allowance, issued in Japanese Continuation Application No. 2014-021052 (Foreign counterpart of U.S. Appl. No. 12/993,163), Aug. 24, 2015.
Office Action dated Nov. 23, 2015, issued in Canadian Application No. 2,833,748 (foreign counterpart of related U.S. Appl. No. 14/112,479).
Office Action issued in counterpart Mexican Application No. MX/a/2010/012691, dated Sep. 24, 2014.
Office Action issued in related Mexican Patent Application No. MX/a/2010/012691, Feb. 10, 2014.
Office Action, dated Jan. 5, 2015, issued in related Japanese Application JP2014-021052 (counterpart to U.S. Appl. No. 12/123,888).
Taiwan Patent Application No. 103109332, Office Action, mailed Aug. 22, 2016.
Taiwan Patent Application No. 103109475, Office Action, mailed Aug. 26, 2016.
Taiwan Patent Application No. 106100512, Office Action, mailed Dec. 4, 2017.

(56) References Cited

OTHER PUBLICATIONS

U.S. Appl. filed Apr. 24, 2012, John B. Slate et al., U.S. Appl. No. 13/454,531.
U.S. Appl. filed Feb. 23, 2017, John B. Slate et al., U.S. Appl. No. 15/440,420.
U.S. Appl. filed Jul. 23, 2008, John B. Slate et al., U.S. Appl. No. 12/178,447.
U.S. Appl. filed May 27, 2011, entitled, "Autoinjector System," of Slate et al., U.S. Appl. No. 12/993,163.
U.S. Appl. filed May 27, 2016, John B. Slate et al., U.S. Appl. No. 15/167,068.
U.S. Appl. filed Oct. 10, 2011, John B. Slate et al., U.S. Appl. No. 13/269,750.
U.S. Appl. No. 29/548,507, Denzer et al., filed Dec. 14, 2015.
U.S. Appl. No. 29/548,508, Denzer et al., filed Feb. 14, 2015.
U.S. Appl. No. 12/123,888, Notice of Allowance, mailed Oct. 3, 2011.
U.S. Appl. No. 12/993,163, Non-Final Office Action, mailed Sep. 11, 2014.
U.S. Appl. No. 12/993,163, Office Action, mailed May 8, 2015.
U.S. Appl. No. 13/269,150, Final Office Action, mailed Oct. 18, 2016.
U.S. Appl. No. 13/269,740, Office Action, mailed Jun. 21, 2013.
U.S. Appl. No. 15/167,068, Final Office Action, mailed Apr. 24, 2019.
U.S. Appl. No. 15/167,068, Non-Final Office Action, mailed Feb. 14, 2020.
U.S. Appl. No. 15/167,068, Notice of Allowance, mailed Jul. 2, 2020.
U.S. Appl. No. 15/782,925, Non-Final Office Action, mailed Oct. 7, 2020.
U.S. Appl. No. 15/782,951, Notice of Allowance, mailed May 20, 2020.
U.S. Appl. No. 15/782,951, Notice of Allowance, mailed Oct. 11, 2019.
U.S. Appl. No. 15/952,296, Non-Final Office Action, mailed Jan. 14, 2020.
U.S. Appl. No. 15/952,296, Notice of Allowance, mailed Jun. 1, 2020.
U.S. Appl. No. 16/026,294, Final Office Action, mailed Jul. 30, 2020.
U.S. Appl. No. 16/026,294, Non-Final Office Action, mailed Mar. 18, 2020.
U.S. Appl. No. 16/026,294, Notice of Allowance, mailed Oct. 16, 2020.
U.S. Appl. No. 16/810,414, Notice of Allowance, mailed Apr. 13, 2022.
U.S. Appl. No. 16/810,414, Notice of Allowance, mailed Jul. 14, 2022.
U.S. Appl. No. 16/832,987, Final Office Action, mailed Jan. 12, 2023.
U.S. Appl. No. 16/832,987, Non-Final Office Action, mailed Sep. 29, 2022.
U.S. Appl. No. 16/832,987, Requirement for Restriction/Election, mailed Apr. 12, 2023.
U.S. Appl. No. 17/003,665, Final Office Action, mailed Jun. 15, 2023.
U.S. Appl. No. 17/003,665, Non-Final Office Action, mailed Feb. 8, 2023.
U.S. Appl. No. 12/123,888, Final Office Action, dated Apr. 8, 2010.
U.S. Appl. No. 12/123,888, Final Office Action, dated Jun. 8, 2011.
U.S. Appl. No. 12/123,888, Non-Final Office Action, dated Dec. 22, 2010.
U.S. Appl. No. 12/123,888, Notice of Allowance, dated Jan. 12, 2012.
U.S. Appl. No. 12/123,888, Office Action, dated Oct. 5, 2009.
U.S. Appl. No. 12/178,447, Final Office Action, dated Mar. 30, 2010.
U.S. Appl. No. 12/178,447, Non-Final Office Action, dated Dec. 22, 2010.
U.S. Appl. No. 12/178,447, Nonfinal Office Action, dated Oct. 15, 2009.
U.S. Appl. No. 12/178,447, Notice of Allowance, date Jun. 24, 2011.
U.S. Appl. No. 12/178,447, Notice of Allowance, dated Apr. 6, 2011.
U.S. Appl. No. 12/454,531, Non-Final Office Action, dated Sep. 13, 2013.
U.S. Appl. No. 12/993,163, Final Office Action, dated Feb. 22, 2016.
U.S. Appl. No. 12/993,163, Non-Final Office Action, dated Dec. 27, 2013.
U.S. Appl. No. 12/993,163, Non-Final Office Action, dated Jul. 28, 2016.
U.S. Appl. No. 13/269,740, Office Action, dated May 20, 2013.
U.S. Appl. No. 13/269,740, Restriction Requirement, dated Apr. 2, 2013.
U.S. Appl. No. 13/269,750, Final Office Action, dated Dec. 26, 2013.
U.S. Appl. No. 13/269,750, Final Office Action, dated Oct. 18, 2016.
U.S. Appl. No. 13/269,750, Non Final Office Action, dated May 3, 2016.
U.S. Appl. No. 13/269,750, Non-Final Office Action, dated Aug. 21, 2014.
U.S. Appl. No. 13/269,750, Non-final Office Action, dated Jun. 21, 2013.
U.S. Appl. No. 13/269,750, Notice of Allowance, dated Feb. 8, 2017.
U.S. Appl. No. 13/269,750, Office Action, dated Aug. 10, 2015.
U.S. Appl. No. 13/269,750, Office Action, dated Mar. 12, 2015.
U.S. Appl. No. 13/269,750, Office Action, dated Nov. 18, 2015.
U.S. Appl. No. 13/454,531, Final Office Action, dated Sep. 23, 2016.
U.S. Appl. No. 13/454,531, Non-Final Office Action, dated Dec. 28, 2012.
U.S. Appl. No. 13/454,531, Non-Final Office Action, dated Mar. 17, 2016.
U.S. Appl. No. 13/454,531, Notice of Allowance, dated Oct. 5, 2015.
U.S. Appl. No. 13/454,531, Office Action, dated Apr. 21, 2015.
U.S. Appl. No. 13/454,531, Office Action, dated Oct. 7, 2014.
U.S. Appl. No. 14/112,479, Final Office Action, dated Feb. 27, 2017.
U.S. Appl. No. 14/112,479, Final Office Action, dated Mar. 29, 2018.
U.S. Appl. No. 14/112,479, Nonfinal Office Action, dated Jul. 12, 2017.
U.S. Appl. No. 14/112,479, Nonfinal Office Action, dated Jul. 29, 2016.
U.S. Appl. No. 14/112,479, Notice of Allowance, dated Jul. 5, 2018.
U.S. Appl. No. 15/167,068, Nonfinal Office Action, dated Oct. 18, 2018.
U.S. Appl. No. 15/167,068, Nonfinal Office Action, dated Oct. 9, 2019.
U.S. Appl. No. 17/813,702, Non-Final Office Action, mailed Mar. 14, 2024.
U.S. Appl. No. 29/750,216, Requirement for Restriction/Election, mailed Jun. 28, 2024.

* cited by examiner

SYSTEM AND METHOD FOR AN INJECTION USING A SYRINGE NEEDLE

CROSS-REFERENCE TO RELATED APPLICATIONS

This application is a continuation of U.S. application Ser. No. 16/832,987, filed Mar. 27, 2020 which is a divisional of U.S. application Ser. No. 15/440,420, filed Feb. 23, 2017, which is a divisional of U.S. application Ser. No. 13/269,750, filed Oct. 10, 2011, now U.S. Pat. No. 9,616,173, which is a continuation of U.S. application Ser. No. 12/178,447, filed Jul. 23, 2008, now U.S. Pat. No. 8,052,645, the entire contents of which are expressly incorporated herein by reference.

FIELD OF THE INVENTION

The present invention pertains generally to systems and methods for injecting fluid medicaments into a patient from a syringe. More particularly, the present invention pertains to auto-injectors that conceal the injection needle of a hypodermic syringe before, and after an injection. The present invention is particularly, but not exclusively, useful as a system and method that employs a bifurcated drive mechanism wherein one motor moves the entire syringe for an injection, and another motor moves the syringe plunger for expelling a fluid medicament from the syringe.

BACKGROUND OF THE INVENTION

In order to inject a fluid medicament into a patient when using a hypodermic syringe, three separate and distinct tasks must be performed. These are: 1) insertion of the needle into the patient; 2) injection of the fluid medicament from the syringe into the patient; and 3) withdrawal of the needle after the injection has been completed. For each task, the magnitude and direction of forces on the syringe, as well as the location of their application, are different from the other tasks. For instance, compare the task of inserting the needle, with the task of injecting the fluid medicament. Insertion of the needle requires that only minimal forces be applied on the syringe, and that they be applied for only a very short period of time. On the other hand, injection of the medicament requires a much greater force be applied. Further, this force must be applied on the plunger of the syringe for what will typically be a relatively longer period of time. In comparison with both of these tasks, needle withdrawal requires the application of a force in the opposite direction.

These, and other similar considerations, become important when the injection process is to be automated.

Springs for generating forces on a syringe in an automated process have been used heretofore for various purposes. A characteristic of springs, however, is that the magnitude and direction of a spring force are not variable. Consequently, springs do not lend themselves for so-called "multi-tasking" operations. This is particularly so where precise control over a syringe injection operation is required, and different magnitude forces are sequentially required in the same direction (e.g. needle insertion and medicament injection).

In addition to the mechanical considerations mentioned above, the design of an auto-injector also requires "user-friendly" considerations. In particular, it is desirable that the injection needle of a syringe be operationally concealed from the view of a user. Preferably, this concealment can be maintained before, during and after an injection procedure. Further, it is desirable that operation of the syringe be limited to only those times when the syringe is properly positioned for an injection.

In light of the above, it is an object of the present invention to provide a two-motor device for performing the injection of a fluid medicament into a patient wherein each motor generates different forces on a hypodermic syringe for different purposes. Another object of the present invention is to provide a reusable injector that can be operationally engaged with a disposable, pre-filled syringe. Still another object of the present invention is to provide an auto-injector system wherein the needle of a pre-filled syringe is operationally concealed and the system is operable only when the injector is properly positioned against the skin of a patient for an injection. Another object of the present invention is to provide a system and a method for automatically injecting a fluid medicament from a pre-filled syringe that is relatively simple to manufacture, is easy to use and is comparatively cost effective.

SUMMARY OF THE INVENTION

In accordance with the present invention an autoinjector system includes a disposable cassette that operates in combination with a reusable injector. Prior to an engagement of the cassette with the injector, however, a pre-filled syringe is mounted and latched onto the cassette. When latched, the syringe is held on the cassette in a so-called "home position". For the present invention, this pre-filled syringe may be of any type syringe well known in the pertinent art that has a fluid chamber with an injection needle at its distal end, and a plunger that can be advanced into the fluid chamber. When the cassette, with syringe, is engaged with the injector, the system is ready for use.

Operation of the system of the present invention requires two separate motors that are individually mounted on the injector. Though they are mechanically independent of each other, the respective operations of these two motors must be coordinated. Specifically, a first motor is used to effect movements of the entire syringe assembly (i.e. syringe chamber, injection needle and plunger are all moved together). On the other hand, a second motor is employed to advance the plunger into the fluid chamber for performing an injection of a fluid medicament.

In a duty cycle of the system, the first motor moves a drive rod into engagement with the syringe. With this engagement, the drive rod also releases the latch that otherwise holds the syringe in its "home position." After the syringe has been released, the first motor then advances the syringe in a distal direction on the cassette. This movement inserts the injection needle into a patient. Further, the first motor can be used to abruptly stop the needle when a specified needle depth has been achieved. The first motor can then be used to help stabilize the needle during an injection of the medical medicament from the syringe.

As mentioned above, the injection of medical medicament from the syringe is accomplished using the second motor. In detail, once the needle has been properly inserted into the patient, the second motor moves a pusher to urge against the plunger of the syringe to advance the plunger into the fluid chamber of the syringe. Importantly, the second motor can be programmed to advance the plunger into the fluid chamber at a predetermined rate(s) for compliance with an injection protocol.

After the injection has been completed, the second motor withdraws the pusher. The first motor is then used again. Specifically, the first motor is now used to withdraw the injection needle from the patient, and to return the syringe to its "home position" on the cassette, where it is re-latched onto the cassette. The cassette can then be removed from the injector and discarded.

In order to control the concerted operations of the first and second motors, the system includes a microcomputer that is mounted on the injector. Importantly, the microcomputer operates the motors with different forces, and at different speeds for different purposes. More specifically, the first motor must operate quickly to insert the needle (e.g. 0.1 to 1 m/s), but it does not require much force to do so. Similarly, needle withdrawal by the first motor requires a minimal force. Unlike the first motor, however, the second motor will typically be required to generate greater forces for the injection of fluid medicament. And, accordingly, it will also typically operate at slower speeds. Further, and most importantly, different injections (i.e. advancements of the syringe plunger by the second motor) may require different injection rates. Thus, the second motor requires speed control provided by the microcomputer.

Together with the components mentioned above, the system of the present invention may, optionally, employ a capacitance skin sensor of a type well known in the pertinent art. If used, such a sensor will allow the user to ascertain whether the system has been properly positioned for an injection. In detail, a metal foil is positioned at the extreme distal end of the injector to establish a capacitance signal whenever the foil is in contact with a skin surface of the patient. The function of this signal is actually two-fold. First, it can be used to prevent initial operation, if the system is not properly positioned. And, second, it can be used to interrupt operation of the system, if it becomes improperly positioned during an injection.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
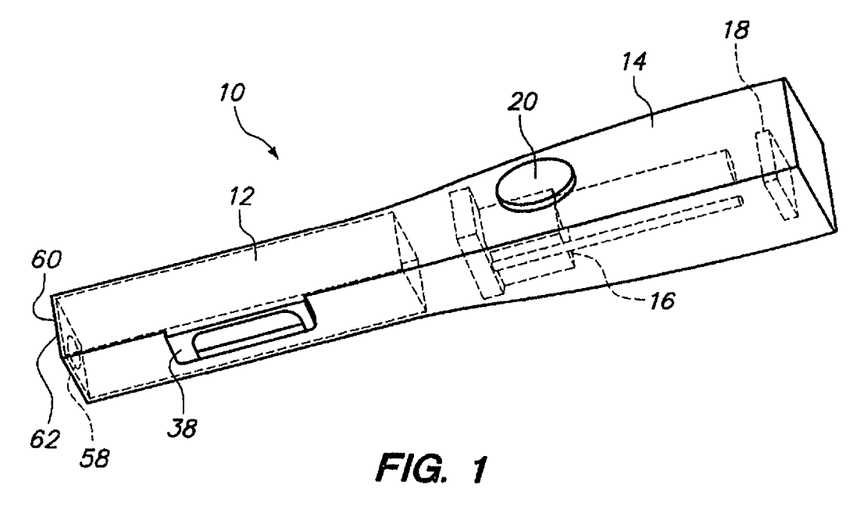
FIG. 1 is a perspective view of an autoinjector system showing a cassette engaged with an injector in accordance with the present invention.

Referring initially to FIG. 1, an autoinjector system in accordance with the present invention is shown and is generally designated 10. As shown, the system 10 essentially includes a disposable cassette 12 and a re-useable injector 14. Further, as shown in phantom in FIG. 1, a drive assembly 16 and a microcomputer 18 are mounted inside the injector 14. As intended for the present invention, the microcomputer 18 is activated by depression of the button 20 on the injector 14. And, when activated, the microcomputer 18 controls the operation of the drive assembly 16 for its interaction with the cassette 12.

Figure 2:
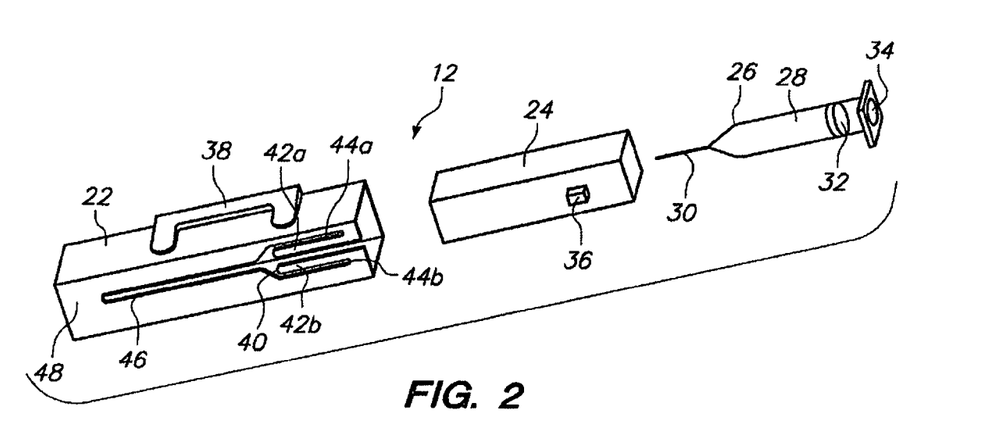
FIG. 2 is an exploded perspective view of the cassette and its component elements for use with the present invention.

In FIG. 2 it will be seen that the cassette 12 includes a housing 22, a sleeve member 24 and a syringe assembly 26. More specifically, the syringe assembly 26 is of a type well-known in the pertinent art that has a syringe chamber 28 for holding a fluid medicament. The syringe assembly 26 will also have an injection needle 30, and a plunger 32 that is moveable within the syringe chamber 28 to expel fluid medicament from the syringe chamber 28 through the injection needle 30. FIG. 2 also shows that the syringe assembly 26 is formed with an orifice 34 that allows for contact with the plunger 32 for the stated purpose. As intended for the present invention, the syringe assembly 26 is fixedly joined with the sleeve member 24 and this combination (i.e. syringe assembly 26 and sleeve member 24) is incorporated with the housing 22 to establish the cassette 12.

Still referring to FIG. 2, it will be seen that the sleeve member 24 includes a protrusion 36. Further, it will be seen that the housing 22 is formed 15 with a fixation member 38 that is dimensioned for engagement with the injector 14 (see FIG. 1). As is to be appreciated by the skilled artisan, the fixation member 38 engages with the injector 14 to position the cassette 12 in an operational alignment with the drive assembly 16. Importantly, the cassette 12 can be fixedly held on the injector 14 during an operation duty cycle of the system 10, and selectively removed from the injector 14 after its use.

FIG. 2 also shows that the housing 22 is formed with a latch mechanism 40. In detail, the latch mechanism 40 includes a pair of opposed, resilient arms 42a and 42b that are respectively formed with a detent 44a and 44b. As shown, the resilient arms 42a and 42b straddle a slot 46 that extends along the side 48 of the housing 22.

An important aspect of the present invention involves the assembly of the cassette 12 into an integral unit. When assembled, it is to be appreciated that the cassette 12 is intended for use only so long as there is fluid medicament in the syringe chamber 28 and, it is thereafter disposable. Prior to assembly, the syringe assembly 26 will have a pre-filled syringe chamber 28 holding a defined dose. The pre-filled syringe assembly 26 is then inserted into the sleeve member 24 where it is fixedly held. Movements of the sleeve member 24 will thus result in a corresponding movement of the syringe assembly 26. The combination (i.e. syringe assembly 26 and sleeve member 24) is then joined with the housing 22. When so joined, the protrusion 36 on 5 sleeve member 24 fits in the detents 44a and 44b between the resilient arms 42a and 42b. Accordingly, the syringe assembly 26 is held on the cassette 12 in a so-called "home position". Importantly, with the syringe assembly 26 in the "home position", the injection needle 30 of the syringe assembly 26 is held, and concealed within the housing 22. In this configuration, the cassette 12 can be engaged with the injector 14 substantially as shown in FIG. 1.

Figure 3A:
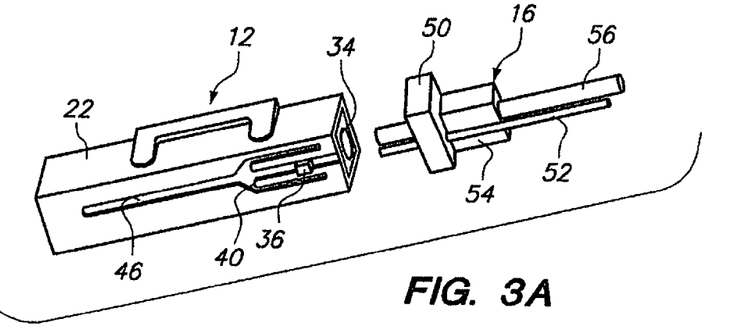
FIG. 3A is a perspective view of a cassette and a drive assembly of the system in position at the beginning and at the end of a duty cycle.
Figure 3B:
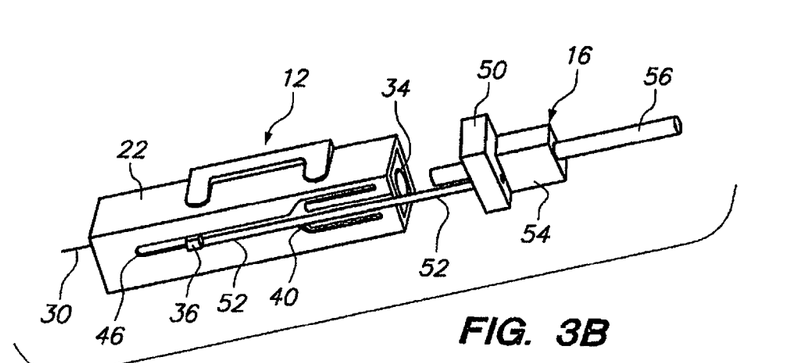
FIG. 3B is a view of the components shown in FIG. 3A with the syringe in the cassette being advanced by a first motor of the drive assembly for insertion of the syringe needle into a patient.
Figure 3C:
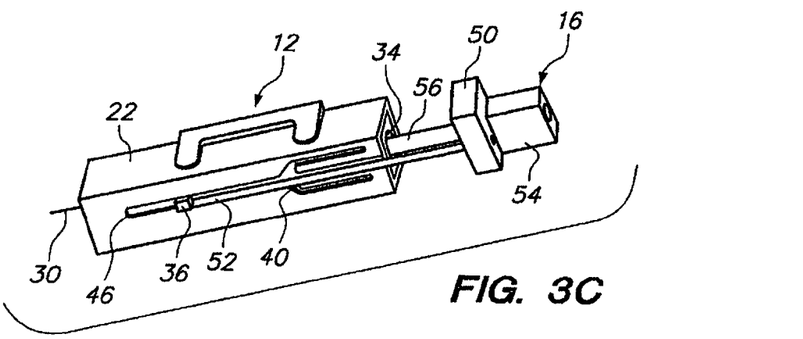
FIG. 3C is a view of the components shown in FIG. 3B with the plunger in the syringe being advanced by a second motor of the drive assembly for injection of a fluid medicament from the syringe into the patient.

For an operation of the system 10, reference is directed collectively to FIGS. 3A, 3B and 3C. Although the injector 14 is not shown in these FIGS., it is to be appreciated that the cassette 12 and the drive assembly 16 are to be considered as being operationally mounted on the injector 14 (i.e. cross-reference FIGS. 3A, 3B and 3C with FIG. 1). Further, in greater detail, the drive assembly 16 is shown in FIG. 3A to include a first motor 50 that is used to move a drive rod 52. Also, a second motor 54 is shown that is used to move a pusher 56. For purposes of the present invention, the motors 50 and 54 can be of any type well known in the pertinent art. Furthermore, the respective movements of drive rod 52 and pusher 56 can be provided by any well-known mechanical device such as a lead screw or a rack-and-pinion. As noted above, the operations of the first motor 50 and the second motor 54 are both controlled by the microcomputer 18.

In overview, a duty cycle for the system 10 can be envisioned as a series of sequential changes in the configuration of cassette 12. For system 10, these configuration changes are caused by separate operations of the first motor 50 and the second motor 54. In compliance with these operations, a complete duty cycle for the system 10 will constitute, in order, configurations shown from FIG. 3A, to FIG. 3B, to FIG. 3C, and then in reverse order from FIG. 3C, back to FIG. 3B and FIG. 3A.

FIG. 3A, shows the cassette 12 with the syringe assembly 26 in its "home position." Importantly, in this "home position" the protrusion 36 on sleeve member 24 is held by the latch mechanism 40 on housing 22. And, consequently, the injection needle 30 of the syringe assembly 26 is held and concealed within the cassette 12. FIG. 3B shows the cassette 12 with the syringe assembly 26 moved into an advanced position wherein the injection needle 30 has been extended from the cassette 12 through a hole 58 at the distal end 60 of the system 10 (see FIG. 1). It is to be appreciated that during the movement from FIG. 3A to FIG. 3B, the first motor 50 advances the drive rod 52. Specifically, with this advancement, the drive rod 52 interacts with latch mechanism 40 to release protrusion 36, and to thereby allow a distal movement of the now "unlatched" syringe assembly 26 and sleeve member 24 on the housing 22. Specifically, this movement is controlled by the microcomputer 18 and is performed with sufficient force to allow the injection needle 30 to penetrate into the tissue of a patient. Preferably, this movement of the syringe assembly 26 from the "home position" (FIG. 3A) to the advanced position (FIG. 3B) is accomplished at a speed of approximately 0.1 to 1 m/s. Further, the first motor 50 can be preprogrammed to stabilize the syringe assembly 26 in its advanced position.

With the syringe assembly 26 in its advanced position (FIG. 3B), microcomputer 18 then activates second motor 54 to move pusher 56 against the plunger 32 in syringe chamber 28 (see FIG. 2). Again, microcomputer 18 is in control and, in this case, can be pre-programmed to advance the plunger 32 at an appropriate speed for injection of the fluid medicament from the syringe chamber 28. At the completion of the injection, the respective configurations of the cassette 12 and the drive assembly 16 are as shown in FIG. 3C. As mentioned above, completion of the injection duty cycle requires the pusher 56 be withdrawn. This withdrawal of the pusher 56 is accomplished by the second motor 54. Once the pusher 56 has been withdrawn (see FIG. 3B), the first motor 50 is again activated to withdraw the drive rod 52. The drive rod 52 then pulls the protrusion 36 back for engagement with the latch mechanism 40, and the syringe assembly 26 is thus returned to its "home position." The cassette 12 can then be removed from the injector 14 and discarded.

As an additional feature of the system 10, a sensor 62 can be provided at the distal end of the injector 14. In particular, the sensor 62 should be positioned adjacent the hole 58 of cassette 12. For purposes of the present invention, the sensor 62 is preferably of a type that will react to capacitance that can be measured between the sensor 62 and the skin of the patient. The purpose of this sensor 62 is to establish that the system 10 is in physical contact with the patient. Specifically, the microcomputer 18 will operate a duty cycle for the system 10 only when such contact is indicated. Otherwise, there can be no operation of the system 10.

While the particular System and Method for an Injection Using a Syringe Needle as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for injecting a fluid medicament into a patient which comprises:
    a cassette having: a housing; a latch mechanism; and a hypodermic syringe, wherein the latch mechanism is operable to selectively hold the hypodermic syringe in the housing;
    an injector configured to be selectively coupled with the cassette such that the cassette is removably received in the injector;
    a first motor mounted on the injector, the first motor being engageable with the cassette for moving the hypodermic syringe relative to the housing between a first position and a second position;
    a second motor mounted on the injector, the second motor being engageable with the hypodermic syringe for expelling the fluid medicament from the hypodermic syringe; and
    a computer mounted on the injector for coordinated control of the first and second motors.

2. The system as recited in claim 1, wherein the hypodermic syringe comprises:
    a syringe chamber for holding the fluid medicament therein;
    an injection needle extending from the syringe chamber; and
    a plunger slidably mounted for advancement into the syringe chamber to expel the fluid medicament therefrom through the injection needle.

3. The system as recited in claim 2, wherein the first position is characterized by the injection needle being withdrawn and concealed within the housing, and the second position is characterized by having the injection needle extend from the housing and from the injector for expelling the fluid medicament from the hypodermic syringe.

4. The system as recited in claim 3, wherein the latch mechanism is operable to fixedly hold the hypodermic syringe in the first position.

5. The system as recited in claim 4, wherein a duty cycle requires, in sequence:
    computer control of the first motor for movement of the hypodermic syringe at a predetermined speed from the first position to the second position;
    computer control of the second motor for advancement of the plunger into the syringe chamber at a predetermined rate for expelling fluid medicament from the hypodermic syringe; and
    computer control of the first motor for withdrawal of the hypodermic syringe from the second position to the first position and for activation of the latch mechanism to fixedly hold the hypodermic syringe in the first position.

6. The system as recited in claim 5, wherein the predetermined speed for advancement of the hypodermic syringe from the first position to the second position is approximately 0.1 to 1 m/s.

7. The system as recited in claim 3, wherein the housing is formed with an orifice to allow for extension of the injection needle from the housing, and the system further comprises a skin sensor mounted on the injector adjacent the orifice to generate a contact signal whenever the orifice is positioned against the skin of the patient.

8. The system as recited in claim 1, wherein the cassette further comprises: a sleeve slidingly coupled to the housing such that the sleeve is selectively movable between the first position and the second position, wherein the hypodermic syringe is fixedly held on the sleeve for movement therewith, and the latch mechanism includes a first part formed on the housing and a second part formed on the sleeve.

9. A system for injecting a fluid medicament into a patient which comprises:
- a hypodermic syringe having a syringe chamber for holding the fluid medicament therein, an injection needle extending from the syringe chamber, and a plunger slidably mounted for advancement into the syringe chamber to expel fluid medicament therefrom through the injection needle;
- a cassette for holding the hypodermic syringe, the cassette being operable such that the hypodermic syringe is selectively moveable between a first position wherein the injection needle is withdrawn and concealed and a second position wherein the injection needle extends from the cassette for expelling the fluid medicament from the hypodermic syringe; and
- an injector configured to be selectively coupled with the cassette such that the cassette is removably received in the injector, the injector comprising a drive means configured to be engaged with the cassette and the hypodermic syringe, the drive means being bifurcated to have a first motor for moving the hypodermic syringe between the first and second positions and a second motor for advancing the plunger into the syringe chamber to expel the fluid medicament when the hypodermic syringe is in the second position.

10. The system as recited in claim 9, wherein the cassette includes:
- a housing; and
- a latch mechanism comprising a portion of the housing operable to hold the hypodermic syringe in the first position.

11. The system as recited in claim 10, wherein the cassette further comprises a sleeve slidingly coupled to the housing such that the sleeve is movable between the first position and the second position, wherein the hypodermic syringe is fixedly held on the sleeve for movement therewith, and the latch mechanism comprises the portion of the housing and a portion of the sleeve.

12. The system as recited in claim 10, wherein the first motor is engageable with the housing for moving the hypodermic syringe between the first and second positions.

13. The system as recited in claim 10, further comprising a computer coupled to the drive means for coordinated control of the first motor and the second motor.

14. The system as recited in claim 13, wherein a duty cycle requires, in sequence: computer control of the first motor for movement of the hypodermic syringe at a predetermined speed from the first position to the second position; computer control of the second motor for advancement of the plunger into the syringe chamber with a predetermined force at a predetermined rate for expelling fluid medicament from the hypodermic syringe; and computer control of the first motor for withdrawal of the hypodermic syringe from the first position to the second position and for activation of the latch mechanism to fixedly hold the hypodermic syringe in the first position.

15. The system as recited in claim 14, wherein the predetermined speed for advancement of the hypodermic syringe from the first position to the second position is approximately 0.1 to 1 m/s.

\* \* \* \* \*